United States Patent
Gargano et al.

(10) Patent No.: US 7,701,570 B2
(45) Date of Patent: Apr. 20, 2010

(54) COLLIMATED LIGHT METHOD AND SYSTEM FOR DETECTING DEFECTS IN HONEYCOMBS

(75) Inventors: Patrick Michael Gargano, Addison, NY (US); Babak Robert Raj, Elmira, NY (US); William Paul Ryszytiwskyj, Corning, NY (US); John Charles Speeckaert, Painted Post, NY (US); David John Worthey, Elmira, NY (US)

(73) Assignee: Corning Incorporated, Corning, NY (US)

(*) Notice: Subject to any disclaimer, the term of this patent is extended or adjusted under 35 U.S.C. 154(b) by 21 days.

(21) Appl. No.: 11/301,570

(22) Filed: Dec. 12, 2005

(65) Prior Publication Data
US 2007/0132988 A1 Jun. 14, 2007

(51) Int. Cl.
*G01N 21/00* (2006.01)

(52) U.S. Cl. .................................. 356/237.6

(58) Field of Classification Search ............. 356/237.6, 356/241.1, 237.1, 336–338, 343, 441
See application file for complete search history.

(56) References Cited

U.S. PATENT DOCUMENTS

| | | | | |
|---|---|---|---|---|
| 4,319,840 A | * | 3/1982 | Kondo et al. ............. | 356/241.1 |
| 4,338,028 A | * | 7/1982 | Tailleur et al. ........... | 356/239.4 |
| 4,556,543 A | * | 12/1985 | Mochida et al. ............. | 422/171 |
| 4,988,887 A | * | 1/1991 | Watanabe et al. ...... | 250/559.16 |
| 5,463,462 A | * | 10/1995 | Ohnishi et al. ............... | 356/521 |
| 6,548,142 B1 | * | 4/2003 | Kar et al. ..................... | 428/116 |
| 6,819,418 B2 | * | 11/2004 | Yoneda ..................... | 356/237.6 |
| 6,891,612 B1 | * | 5/2005 | Koike et al. .............. | 356/237.6 |
| 7,289,200 B1 | * | 10/2007 | Strafford et al. ......... | 356/237.1 |
| 2003/0174320 A1 | * | 9/2003 | Yokoyama et al. ....... | 356/237.6 |
| 2005/0106356 A1 | * | 5/2005 | Ikeshima ..................... | 428/116 |
| 2006/0151926 A1 | * | 7/2006 | Zoeller ....................... | 264/603 |
| 2007/0091309 A1 | * | 4/2007 | Kondo ........................ | 356/364 |

FOREIGN PATENT DOCUMENTS

| | | |
|---|---|---|
| JP | 58-155343 | 9/1983 |
| JP | 05-264459 | 10/1993 |
| JP | 2004-037248 | 2/2004 |
| JP | 2005-274179 | 10/2005 |
| WO | WO2005/040773 * | 5/2005 |

* cited by examiner

*Primary Examiner*—Tarifur Chowdhury
*Assistant Examiner*—Tara S Pajoohi
(74) *Attorney, Agent, or Firm*—Joseph M. Homa

(57) ABSTRACT

A system and method for detecting defective cells in honeycomb bodies which includes a light source which launches and couples light into cells at a first end face of the honeycomb body, and a projection medium which receives the light at a second end face of the honeycomb body. The light source is preferably a collimated light source.

14 Claims, 3 Drawing Sheets

COLLIMATED LIGHT METHOD AND SYSTEM FOR DETECTING DEFECTS IN HONEYCOMBS

BACKGROUND OF THE INVENTION

The invention relates generally to inspection of wall-flow particulate filters, and particularly to a method and apparatus for detecting defects in a wall-flow particulate filter.

Solid particulates in fluids such as exhaust gas are typically removed using wall-flow particulate filters having a honeycomb structure. FIG. 1 illustrates a typical wall-flow, honeycomb, particulate filter 100. The honeycomb filter 100 has an inlet end face 102 and an outlet end face 104 and an array of porous walls 106 extend longitudinally from the inlet end face 102 to the outlet end face 104. The porous walls 106 intersect each other to define a grid of generally parallel inlet cells 108 and outlet cells 110. The outlet cells 110 are preferably closed with plugs 112 where they adjoin the inlet end face 102 and open where they adjoin the outlet end face 104. Similarly, the inlet cells 108 are preferably closed with plugs (not shown) where they adjoin the outlet end face 104 and open where they adjoin the inlet end face 102. In a typical cell structure, each inlet cell 108 is bordered on one or more sides by outlet cells 110 and vice versa, preferably in a checkerboard pattern. The inlet and outlet cells 108, 110 may have a square cross-section as shown in FIG. 1 or may have other cell geometry, e.g., rectangle, triangle or hexagon.

In operation, the honeycomb filter 100 is installed in an appropriate can and inserted into the exhaust system of a vehicle equipped with a diesel engine. During operation of the vehicle, diesel exhaust is directed at the inlet end face 102 of the honeycomb filter 100. The diesel exhaust flows into the inlet cells 108 of the honeycomb filter 100, passes through the porous walls 106 into the outlet cells 110, and exits the filter at the outlet end face 104. The porous walls 106 retain a desired portion of the solid particulates in the exhaust.

Filtration efficiencies up to and in excess of 90% by weight of the diesel exhaust particulates can be achieved with honeycomb filters such honeycomb filters 100. However, the filtration efficiency achievable can be dramatically reduced if there are leaks in the honeycomb filter. Such leaks may be due to straight-through defects (cracks, tears, large pores) in the interior porous walls and/or defects in the plugs of the filter (defects include missing plugs). Such defects allow the exhaust gas to pass through the interior walls and/or plugs of the filter uninhibitedly. It is desirable to find such defects and repair them, where possible, prior to using the honeycomb filter in particulate filtration applications. In cases where the honeycomb filters are made by extrusion from ceramic materials, such as cordierite, aluminum titanate and silicon carbide, the defects may be detected before or after firing of the honeycomb body. In the former case, the interior walls are nonporous. In the latter case, the interior walls are porous. Typically, it is easier to repair defects while the honeycomb body is unfired or green.

From the foregoing, it should be apparent there is a need for an improved method of detecting straight-through defects in honeycomb filters which reduce inspection time and improve detection reliability.

SUMMARY OF THE INVENTION

In one aspect, the invention is a system of detecting defective cells in a honeycomb body which comprises a light source, preferably a substantially collimated light source, which launches and couples light into cells at a first end face of the honeycomb body, and a projection medium which receives the light at a second end face of the honeycomb body. Patterns of light on the projection medium are indicative of defective cells and may be imaged by an observer and then possibly repaired.

In another aspect, the invention is a method of detecting defective cells in a honeycomb body which comprises launching light into cells at a first end face of a honeycomb body, and receiving the light at a second end face of the honeycomb body. The light emerges at the second end face at locations corresponding to defective cells in the honeycomb body. The light may be received on a projection medium or otherwise imaged by an observer. Preferably, the light comprises substantially collimated light.

Other features and advantages of the invention will be apparent from the following description and the appended claims.

DETAILED DESCRIPTION OF THE INVENTION

The invention will now be described in detail with reference to a few preferred embodiments, as illustrated in accompanying drawings. In the following description, numerous specific details are set forth in order to provide a thorough understanding of the invention. It will be apparent, however, to one skilled in the art, that the invention may be practiced without some or all of these specific details. In other instances, well-known features and/or process steps have not been described in detail in order to not unnecessarily obscure the invention. The features and advantages of the invention may be better understood with reference to the drawings and discussions that follow.

Figure 1:
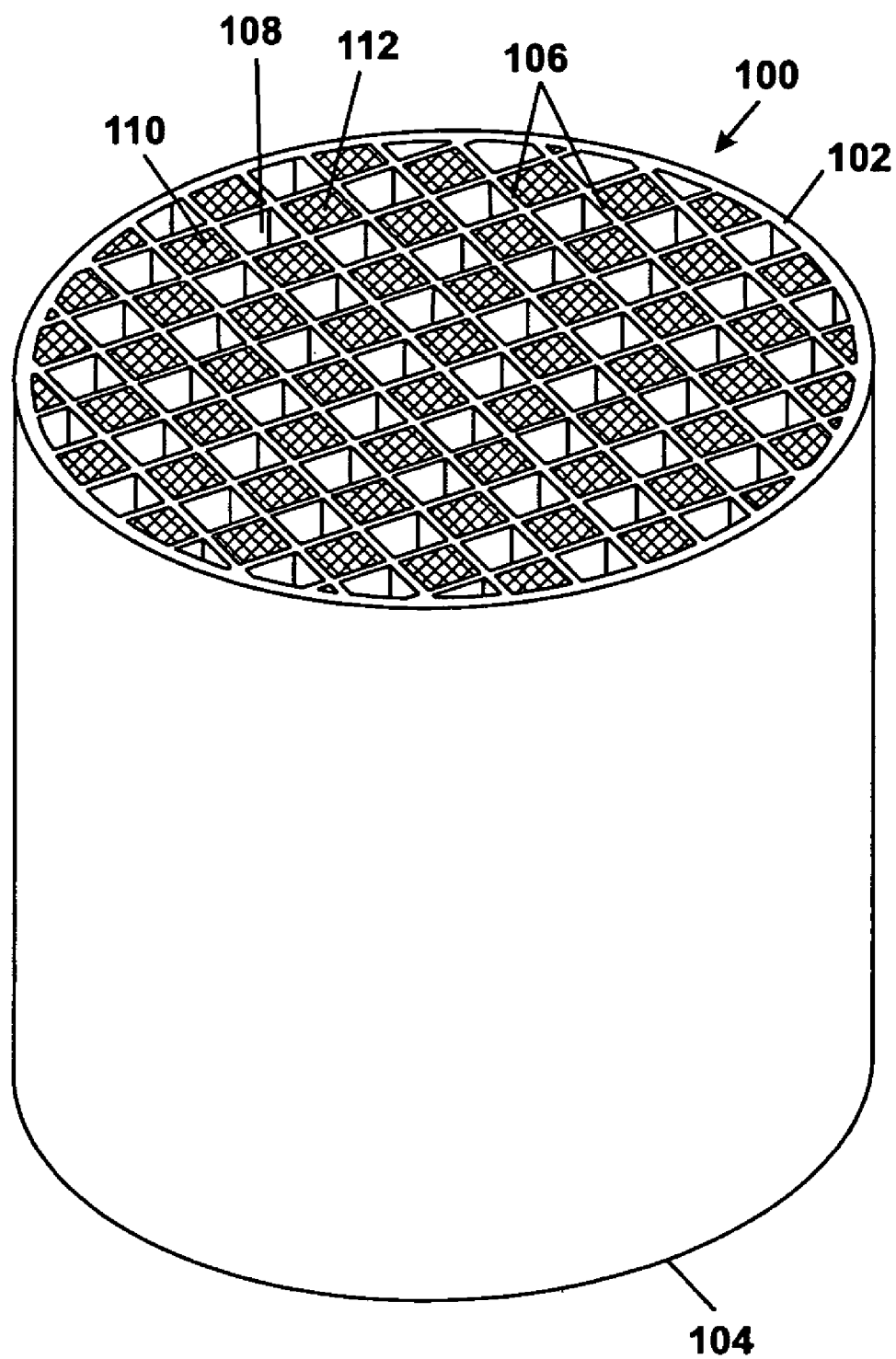
FIG. 1 is a perspective view of a prior-art wall-flow honeycomb filter.
Figure 2A:
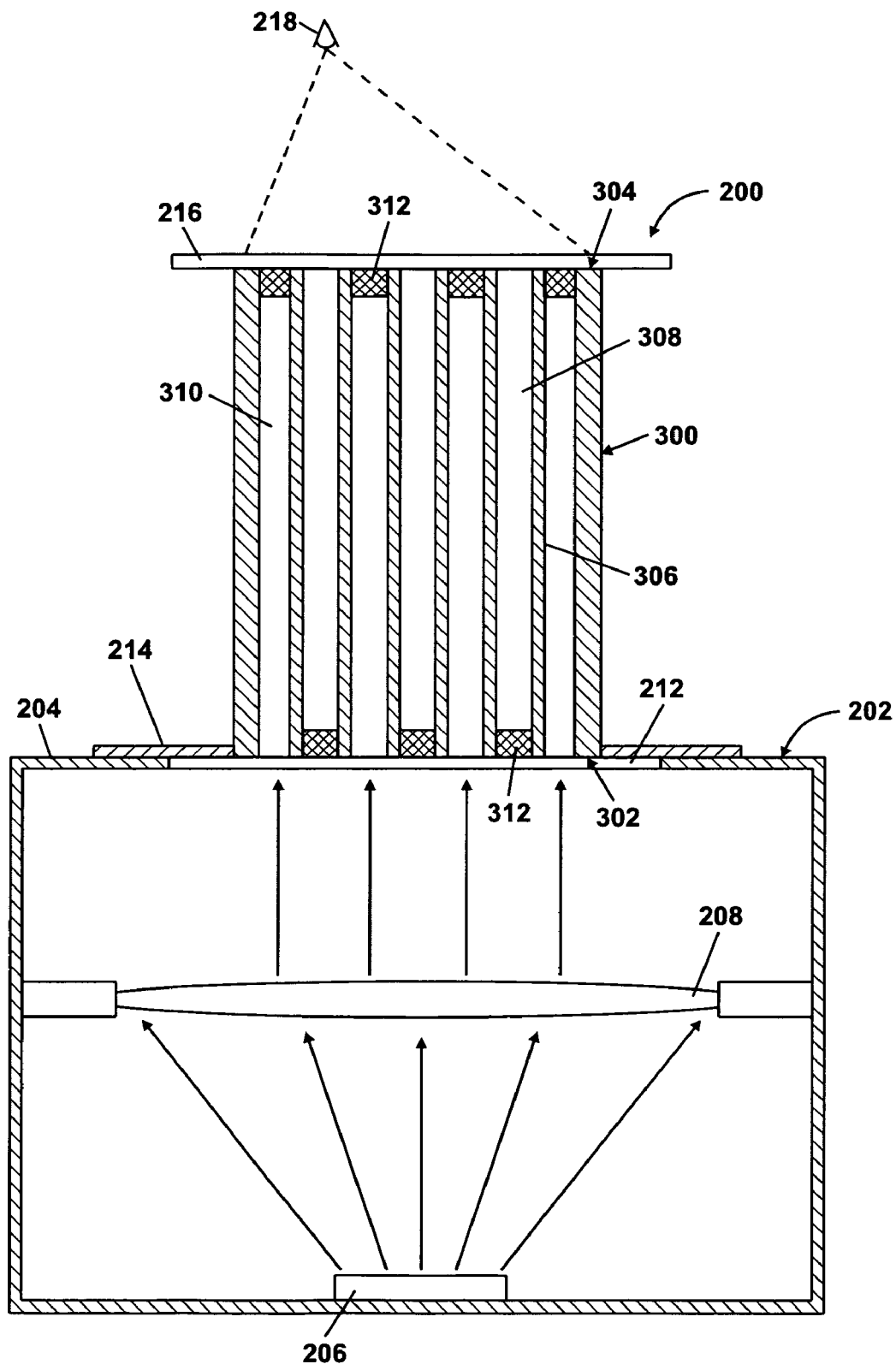
FIGS. 2A and 2B illustrate a side cross-sectioned view of a system for detecting straight-through defects in a honeycomb body according to the invention.

FIG. 2A is a schematic of a system 200 for detecting defective cells in a honeycomb body 300. The honeycomb body 300 has end faces 302, 304 and preferably parallel thin interior walls 306 extending between the end faces 302, 304. For the purpose of detecting straight-through defects in the honeycomb body 300, the interior walls 306 may be porous or nonporous. For solid particulate filtration purposes, the walls 306 are porous, such as in a fired honeycomb body. The walls 306 intersect to define a grid of inlet and outlet cells 308, 310. Plugs 312 are preferably inserted in the ends of the cells 308 adjoining the end face 302 and the ends of the cells 310 adjoining the end face 304, respectively, while the ends of the cells 308 adjoining the end face 304 and the ends of the cells 310 adjoining the end face 302 are left unplugged. The material of the plugs 312 may be any suitable sealing/filler material, e.g., a ceramic material mixed with a binder and plasticizer. Upon firing, the plugs 312 may also be porous.

The honeycomb body 300 may be made by extrusion or other suitable process. Typically, the extrusion material is a plasticized ceramic-forming material, which forms for example, cordierite, aluminum titanate or silicon carbide, but could also be glass, glass-ceramic, plastic, or metal material. In the case of ceramic-forming materials, they may be mixed with a pore former, such as graphite or starch, and with cellulosic binder materials, and then fired to burn out the pore former and binder, thereby forming a solid ceramic body having porous interior walls. Preferably, the thickness and porosity of the interior walls 306 are such that the structural integrity of the honeycomb body 300 is not compromised. For example, the walls 306 may incorporate pores having median pore diameters in the range of 1 to 60 μm, more preferably in a range from 10 to 50 μm. In general, the thickness of the walls 306 can vary upwards from the minimum dimension providing structural integrity of about 0.010 in. (about 0.25 mm) to about 0.060 in. (1.5 mm). Typically, a wall thickness in a range from about 0.010 to 0.030 in (about 0.25 to 0.76 mm) is most often selected at the preferred cellular density. The honeycomb body 300 may have a cellular density between about 10 and 350 cells/in$^2$ (about 1.5 to 52.5 cells/cm$^2$), more typically between about 100 and 350 cells/in$^2$ (about 15.5 to 52.5 cells/cm$^2$).

In operation, the honeycomb body 300 is mounted on a collimated light box 202. The collimated light box 202 includes a housing 204 inside of which is mounted a light source 206 and a collimator such as a collimating lens 208. Typically, the light source 206 is a diffuse light source. Any suitable diffuse light source, such as a white light source, may be used. For example, the light source may be a halogen light bulb having a power of between about 30 and 1200 watts. A 50 watt source works well when the apparatus is housed in a dark room. The collimating lens 208 converts the divergent beams from the diffuse source into a substantially collimated beam. Any suitable collimating lens may be used. In one example, the collimating lens 208 is a Fresnel lens plate. However, any lens having the functionality of a Fresnel lens, i.e., it collimates light may be employed. A Fresnel lens plate having a focal length of about 24", 200 grooves/inch, and a 14 inch diameter works well for most filter sizes. It should be recognized that the collimated light source may be any source that provides a substantially collimated light to the first end. The degree of collimation required depends on the substrate's length and cell geometry. The light needs to be collimated such that it passes though the cell. An end of the housing 204 is provided with a window 212, preferably made of a planar and non-dispersive, non-light scattering transparent material, such as a tempered glass pane. The plane of the window 212 is preferably substantially perpendicular to the path of the collimated light. This is best accomplished by aligning the window with an optical plane of the collimating lens 208, i.e., the window 212 and the collimating lens 208 are preferably substantially parallel. The honeycomb body 300 is supported on the window 212 so that light from the collimated light box 202 is directly coupled into the cells in the honeycomb body 300. A light block 214 such as an opaque medium covers the exposed portions of the window 212, and closely abuts the outer periphery of the honeycomb 300 thereby subjecting the substantially collimated light from the collimated light box 202 to the end face 302 of the honeycomb body 300. Optionally, the light block 214 may be an air bladder that holds the filter about its periphery. The light block may take any form that substantially prevents or minimizes light from passing about the filter.

To detect straight-through defects in the honeycomb body 300, the collimated light box 202 directs substantially collimated light at the end face 302 of the honeycomb body 300. The light from the light box 202, being substantially collimated, is efficiently coupled and launched into every cell 310 in the honeycomb body 300. Light may also be launched into the cells 308 if there are defects in the plugs 312 at the end face 302. The collimated light launched into the honeycomb body 300 emerges at the end face 304 through cells that are defective. A projection medium 216 is mounted on the end face 304 and preferably rests upon and is in contact with the end face. The projection medium 216 receives the light emerging from the end face 304, wherein such light may be observed by an observer 218. In one example, the projection medium 216 is made of a translucent material, such as paper or a film. In another embodiment, the projection medium is a screen, preferably stretched over a frame. The screen is most preferably a finely woven screen of polyester monofilament material having a woven density of about 460 threads/inch and a thread diameter of about 31 μm. The observer 218 can thus instantly visualize the location of all the straight-through defects in the honeycomb body 300 from virtually any position by observing the image formed on the projection medium 216. The defects appear as light spots on the projection medium 216. Defects such as large holes in plugs, partial fills, and missing plugs appear as bright spots. Light spots appearing blotchy at locations corresponding to plugs 312 may be indicative of inconsistency defects in the plug. Such inconsistency defects may be attributed to plug depth, plug material density, air bubbles in the plug, nearly complete fills, and combinations thereof. Missing peripheral plugs are very readily detected. Once defects in the plugs are found, the defects may be repaired/reworked or the filter may be otherwise rejected.

The collimated light box 202 ensures that light is properly launched into the cells in the honeycomb body 300 simultaneously, including into the cells at or near the periphery of the honeycomb body 300, and that the light is guided toward the projection medium 216. As a result, the optical axis of the observer 218 does not have to be aligned with every cell in the honeycomb body 300 in order to determine whether or not the cell has a straight-through defect. Further, the observation of the projection image may be by an observer 218 who may be a human, or an imaging device. The latter may be employed to enable an automated method of detecting and repairing defective cells in the honeycomb body 300.

Figure 2B:
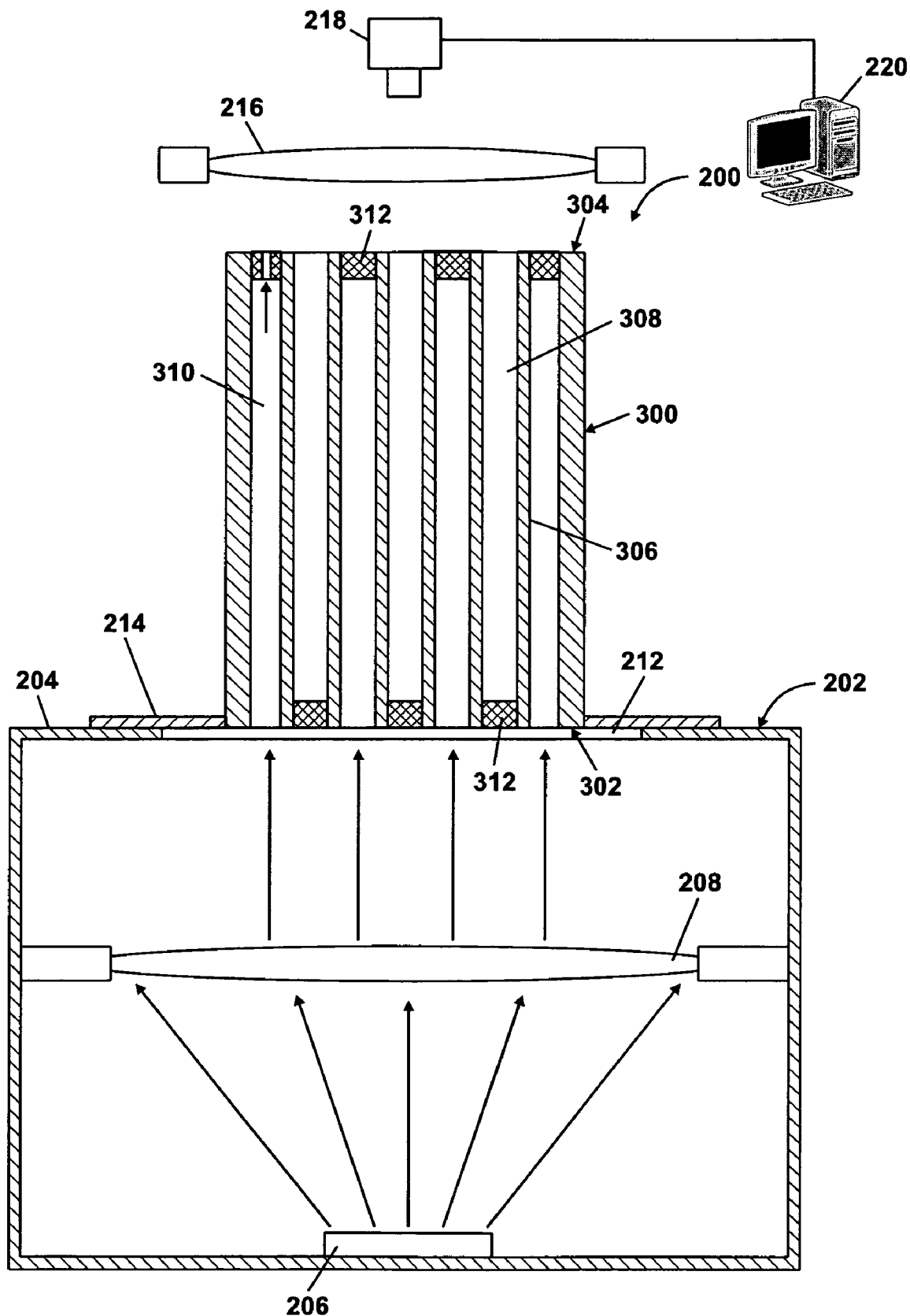

FIG. 2B shows the observer 218 as an imaging device, such as a camera. The imaging device 218 is coupled to a processor 220, which receives images from the imaging device 218 and processes the images to determine the x-y coordinates of defective cells across the end face 304 of the honeycomb body 300. The defective cells in the honeycomb body 300 may then be repaired. In this example, the projection medium 216 is depicted as a lens that focuses the substantially collimated light coming from the end face 304 of the honeycomb body 300 into the imaging device 218. Alternatively, the projection medium 216 may be a translucent material as previously discussed, and the imaging device 218 may include an optical device, such as a camera, to capture a quality image of the translucent material.

The invention typically provides the following advantages. The system 200 enables instant and simultaneous detection of "straight-thru" defective cells regardless of their location in the honeycomb body 300. It is especially useful for detecting unplugged edge cells (those located within one cell from the filter periphery or skin). The system 200 also enables instant detection of plug consistency. The system eliminates the need for alignment of the optical axis of the observer with the defective cells. The system 200 therefore increases product throughput and improves detection reliability. The method of detecting defective cells using the system is effectively operator-independent, that is, detection results do not vary from operator to operator.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A system for detecting defective cells in a ceramic honeycomb body having an outer periphery and first and second opposite end faces each with open and plugged cells formed respectively by first and second sets of plugs, the system comprising:
   a housing having an end provided with a transparent window that serves as a mounting surface upon which the first end face rests and contacts, and that is not part of or fixed to the honeycomb body, and a light block arranged adjacent the transparent window and sized to the honeycomb body outer periphery, the housing further having an inside that contains a light source which launches substantially collimated light through the transparent window and into the first end face of the honeycomb body and
   a projection medium disposed adjacent and in contact with the second end face of the honeycomb body, wherein the projection medium receives light emerging from the second end face through at least one defect in at least one of the first and second sets of plugs, and wherein the projection medium comprises a translucent material or a woven screen upon which said received light appears visible to an observer and is representative of the at least one defect.

2. The system of claim 1 wherein the light source comprises a collimator.

3. The system of claim 1 wherein the light source comprises a diffuse light source and a collimating lens, the diffuse light source and collimating lens being positioned such that light passes from the diffuse light source to the first end face through the collimating lens.

4. The system of claim 3 wherein the collimating lens is a Fresnel lens.

5. The system of claim 1 wherein the transparent window is substantially parallel to a focal plane of a collimating lens.

6. The system of claim 1 wherein the light block comprises an opaque medium.

7. The method of claim 1 wherein the translucent material is paper or film.

8. The method of claim 1, wherein the observer includes an imaging device or a human.

9. A method of detecting a defective plug in a ceramic honeycomb filter body, comprising the steps of:
   launching substantially collimated light into a first end face of the honeycomb body which has both open and plugged cells formed by a first set of plugs, the first end face of the honeycomb body resting upon and being in contact with a transparent window that is not part of or attached to the honeycomb filter body;
   receiving the light at a second end face of the honeycomb body also having open and plugged cells formed by a second set of plugs, wherein the light emerges at the second end face at locations corresponding to the defective plug in one of the first and second sets of plugs; and
   receiving the emerging light by a projection medium that contacts the second end face of the honeycomb body, wherein the projection medium comprises a translucent material or a woven screen upon which the received light is visible as a light spot to an observer; and
   repairing the defective plug.

10. The method of claim 9 wherein the step of launching light comprises passing light from a light source to the first end face through a collimator.

11. The method of claim 10 wherein the collimator is a collimating lens.

12. The method of claim 9 wherein the projection medium comprises paper or film.

13. The method of claim 9, wherein the observer includes an imaging device or a human.

14. The method of claim 9, wherein the honeycomb body has an outer periphery and further comprising covering an exposed portion of the transparent window with a light block that closely abuts the honeycomb outer periphery.

* * * * *